United States Patent
Gillespie, III (10) Patent No.: US 8,123,724 B2
(45) Date of Patent: *Feb. 28, 2012

(54) AUTO-INJECTION SYRINGE HAVING VENT DEVICE

(75) Inventor: Richard David Gillespie, III, Athens, TX (US)

(73) Assignee: West Pharmaceutical Services of Delaware, Inc., Lionville, PA (US)

( * ) Notice: Subject to any disclaimer, the term of this patent is extended or adjusted under 35 U.S.C. 154(b) by 1216 days.

This patent is subject to a terminal disclaimer.

(21) Appl. No.: 11/458,114

(22) Filed: Jul. 18, 2006

(65) Prior Publication Data

US 2007/0078394 A1    Apr. 5, 2007

Related U.S. Application Data

(63) Continuation-in-part of application No. 11/296,973, filed on Dec. 8, 2005, now Pat. No. 7,674,246.

(60) Provisional application No. 60/700,219, filed on Jul. 18, 2005, provisional application No. 60/634,486, filed on Dec. 9, 2004.

(51) Int. Cl.
*A61M 5/20* (2006.01)
*A61M 5/315* (2006.01)
*A61M 5/00* (2006.01)
*A61M 5/32* (2006.01)
*A61M 5/24* (2006.01)

(52) U.S. Cl. ........ 604/134; 604/218; 604/187; 604/201; 604/181; 604/192; 604/203; 604/244; 604/264

(58) Field of Classification Search .................. 604/218, 604/134, 187, 201, 135, 157, 244, 203, 82–92, 604/200, 194, 181, 192, 264; 251/309
See application file for complete search history.

(56) References Cited

U.S. PATENT DOCUMENTS 2,561,233 A   7/1951   Ryan et al.
(Continued)

FOREIGN PATENT DOCUMENTS

CN        1011761 A       6/1987
(Continued)

OTHER PUBLICATIONS

Office Action Issued Apr. 17, 2009 in related U.S. Appl. No. 11/296,973.

(Continued)

*Primary Examiner* — Kevin C Sirmons
*Assistant Examiner* — Bradley Thomas, Jr.
(74) *Attorney, Agent, or Firm* — Panitch Schwarze Belisario & Nadel LLP (57) ABSTRACT

An auto-injection syringe is provided that includes an injection assembly and a retraction assembly operatively securable to the injection assembly. The retraction assembly includes a hypodermic needle having a needle hub, an end cap having a lower seal through which a portion of the hypodermic needle can pass, a retraction spring disposed between the needle hub and the end cap and maintained in a partially compressed condition therebetween, an upper seal urged against a facially sealing surface of the retraction assembly by the force of the retraction spring on the needle hub so that a sealed area is defined between the upper and lower seals, and a vent device in fluid communication with the sealed area for pressure equalization between the sealed area and an exterior of the retraction assembly.

20 Claims, 4 Drawing Sheets

U.S. PATENT DOCUMENTS

| | | | |
|---|---|---|---|
| 3,306,290 A | | 2/1967 | Weltman |
| 3,572,336 A | | 3/1971 | Hershberg |
| 3,705,582 A | | 12/1972 | Stumpf et al. |
| 3,707,968 A | | 1/1973 | Koenig |
| 3,708,089 A | | 1/1973 | Holder et al. |
| 3,834,387 A | | 9/1974 | Brown |
| 3,901,402 A | | 8/1975 | Ayres |
| 4,059,109 A | | 11/1977 | Tischlinger |
| 4,445,895 A | | 5/1984 | Margulies |
| 4,542,749 A | | 9/1985 | Caselgrandi et al. |
| 4,581,016 A | | 4/1986 | Gettig |
| D286,164 S | | 10/1986 | Tinz |
| D287,603 S | | 1/1987 | Bruhn |
| 4,643,721 A | | 2/1987 | Brunet |
| 4,689,042 A | | 8/1987 | Sarnoff et al. |
| 4,755,169 A | | 7/1988 | Sarnoff et al. |
| 4,767,413 A | | 8/1988 | Haber et al. |
| 4,795,444 A | | 1/1989 | Hasegawa et al. |
| 4,820,286 A | | 4/1989 | van der Wal |
| 4,822,340 A | * | 4/1989 | Kamstra ............. 604/135 |
| 4,861,335 A | | 8/1989 | Reynolds |
| 4,886,495 A | | 12/1989 | Reynolds |
| 4,898,580 A | | 2/1990 | Crowley |
| 4,969,877 A | | 11/1990 | Kornberg |
| 4,998,922 A | | 3/1991 | Kuracina et al. |
| 5,045,058 A | * | 9/1991 | Demetrakopoulos ......... 604/515 |
| 5,049,133 A | | 9/1991 | Villen Pascual |
| 5,085,641 A | | 2/1992 | Sarnoff et al. |
| 5,085,642 A | | 2/1992 | Sarnoff et al. |
| 5,092,843 A | | 3/1992 | Monroe et al. |
| 5,102,393 A | | 4/1992 | Sarnoff et al. |
| 5,120,310 A | | 6/1992 | Shaw |
| 5,137,511 A | | 8/1992 | Reynolds |
| 5,169,385 A | * | 12/1992 | Turnbull ............. 604/32 |
| 5,176,657 A | | 1/1993 | Shields |
| 5,188,613 A | | 2/1993 | Shaw |
| D339,606 S | | 9/1993 | Podobrin |
| 5,267,961 A | | 12/1993 | Shaw |
| 5,295,965 A | * | 3/1994 | Wilmot ............. 604/136 |
| 5,300,030 A | | 4/1994 | Crossman et al. |
| 5,324,273 A | | 6/1994 | Discko, Jr. |
| 5,358,489 A | | 10/1994 | Wyrick |
| 5,364,363 A | | 11/1994 | Pearson et al. |
| 5,383,865 A | | 1/1995 | Michel |
| 5,385,551 A | | 1/1995 | Shaw |
| 5,389,076 A | | 2/1995 | Shaw |
| 5,391,151 A | | 2/1995 | Wilmot |
| 5,411,487 A | | 5/1995 | Castagna |
| 5,411,489 A | | 5/1995 | Pagay et al. |
| 5,413,564 A | | 5/1995 | Silver et al. |
| 5,423,758 A | | 6/1995 | Shaw |
| 5,425,715 A | * | 6/1995 | Dalling et al. ............. 604/136 |
| 5,466,223 A | | 11/1995 | Bressler et al. |
| 5,531,255 A | | 7/1996 | Vacca |
| 5,540,664 A | | 7/1996 | Wyrick |
| 5,545,145 A | | 8/1996 | Clinton et al. |
| 5,578,011 A | | 11/1996 | Shaw |
| 5,599,309 A | | 2/1997 | Marshall et al. |
| 5,620,421 A | | 4/1997 | Schmitz |
| 5,632,733 A | | 5/1997 | Shaw |
| 5,637,092 A | | 6/1997 | Shaw |
| 5,643,214 A | | 7/1997 | Marshall et al. |
| 5,665,071 A | | 9/1997 | Wyrick |
| 5,674,204 A | | 10/1997 | Chanoch |
| 5,685,846 A | | 11/1997 | Michaels, Jr. |
| 5,688,251 A | | 11/1997 | Chanoch |
| 5,695,472 A | | 12/1997 | Wyrick |
| 5,779,677 A | | 7/1998 | Frezza |
| 5,779,679 A | | 7/1998 | Shaw |
| 5,810,775 A | | 9/1998 | Shaw |
| 5,817,058 A | | 10/1998 | Shaw |
| RE35,986 E | | 12/1998 | Ritson et al. |
| 5,860,961 A | | 1/1999 | Gettig |
| 5,873,462 A | | 2/1999 | Nguyen et al. |
| 5,921,966 A | | 7/1999 | Bendek et al. |
| 5,931,817 A | | 8/1999 | Nguyen et al. |
| 5,941,857 A | | 8/1999 | Nguyen et al. |
| 5,944,700 A | | 8/1999 | Nguyen et al. |
| D414,201 S | | 9/1999 | Larson et al. |
| 5,957,896 A | | 9/1999 | Bendek et al. |
| 5,957,897 A | | 9/1999 | Jeffrey |
| D414,807 S | | 10/1999 | Baudino et al. |
| 5,961,495 A | | 10/1999 | Walters et al. |
| 5,989,220 A | | 11/1999 | Shaw et al. |
| 5,997,512 A | | 12/1999 | Shaw |
| 6,001,082 A | | 12/1999 | Dair et al. |
| 6,015,438 A | | 1/2000 | Shaw |
| D423,577 S | | 4/2000 | Baudino et al. |
| D425,120 S | | 5/2000 | Ramil |
| 6,086,563 A | | 7/2000 | Moulton et al. |
| 6,095,814 A | | 8/2000 | Petrich et al. |
| 6,099,503 A | | 8/2000 | Stradella |
| 6,149,623 A | | 11/2000 | Reynolds |
| 6,183,445 B1 | | 2/2001 | Lund et al. |
| 6,200,627 B1 | | 3/2001 | Lubrecht |
| 6,210,315 B1 | | 4/2001 | Andrews et al. |
| 6,210,369 B1 | | 4/2001 | Wilmot et al. |
| 6,210,371 B1 | | 4/2001 | Shaw |
| 6,213,597 B1 | | 4/2001 | Liu |
| 6,221,046 B1 | | 4/2001 | Burroughs et al. |
| 6,221,053 B1 | | 4/2001 | Walters et al. |
| 6,221,055 B1 | | 4/2001 | Shaw et al. |
| D441,398 S | | 5/2001 | Owen et al. |
| 6,248,095 B1 | | 6/2001 | Giambattista et al. |
| D446,242 S | | 8/2001 | Stukenkemper |
| 6,277,099 B1 | | 8/2001 | Strowe et al. |
| D452,271 S | | 12/2001 | Owen et al. |
| 6,328,715 B1 | | 12/2001 | Dragan et al. |
| 6,346,094 B2 | | 2/2002 | West et al. |
| 6,349,850 B1 | | 2/2002 | Cheikh |
| 6,387,078 B1 | * | 5/2002 | Gillespie, III ............. 604/181 |
| 6,413,237 B1 | | 7/2002 | Caizza et al. |
| 6,494,863 B1 | | 12/2002 | Shaw et al. |
| 6,572,584 B1 | | 6/2003 | Shaw et al. |
| 6,638,244 B1 | | 10/2003 | Reynolds |
| 6,689,118 B2 | | 2/2004 | Alchas et al. |
| 6,793,646 B1 | | 9/2004 | Giambattista et al. |
| 6,796,967 B2 | | 9/2004 | Jensen |
| 6,802,828 B2 | | 10/2004 | Reynolds |
| 2001/0002434 A1 | | 5/2001 | Lubrecht |
| 2001/0029354 A1 | | 10/2001 | Rolle et al. |
| 2001/0039400 A1 | | 11/2001 | Lubrecht |
| 2002/0010430 A1 | | 1/2002 | Dragan et al. |
| 2002/0164265 A1 | | 11/2002 | Hetzler |
| 2002/0177819 A1 | | 11/2002 | Barker et al. |
| 2003/0083621 A1 | | 5/2003 | Shaw et al. |
| 2003/0088216 A1 | | 5/2003 | Py |
| 2003/0100866 A1 | | 5/2003 | Reynolds |
| 2003/0130626 A1 | | 7/2003 | VanTassel et al. |
| 2003/0187388 A1 | | 10/2003 | Sharon et al. |
| 2004/0024367 A1 | | 2/2004 | Gilbert |
| 2004/0111064 A1 | | 6/2004 | Asbaghi |
| 2005/0049551 A1 | | 3/2005 | Kirchhofer |
| 2005/0113763 A1 | | 5/2005 | Reynolds |
| 2006/0178629 A1 | | 8/2006 | Gillespie et al. |
| 2006/0178631 A1 | | 8/2006 | Gillespie et al. |

FOREIGN PATENT DOCUMENTS

| | | |
|---|---|---|
| JP | 59-172438 A | 9/1984 |
| JP | 62-117566 A | 5/1987 |
| JP | 63-290577 A | 11/1988 |
| JP | 2584462 B2 | 2/1997 |
| JP | 10057483 A | 3/1998 |
| JP | 2000-334041 A | 12/2000 |
| JP | 2002-153557 A | 5/2002 |
| JP | 2003-199825 A | 7/2003 |
| WO | 8902287 A1 | 3/1989 |
| WO | 9535126 A1 | 12/1995 |
| WO | 2006063124 A2 | 6/2006 |

OTHER PUBLICATIONS

Office Action Issued Mar. 29, 2006 in related U.S. Appl. No. 11/297,159.

Office Action Issued Apr. 11, 2007 in related U.S. Appl. No. 11/297,159.

Office Action Issued Dec. 31, 2007 in related U.S. Appl. No. 11/297,159.

Office Action Issued Nov. 13, 2008 in related U.S. Appl. No. 11/297,159.
Office Action Issued Nov. 1, 2006 in related U.S. Appl. No. 11/297,225.
Office Action Issued Jun. 30, 2009 in related U.S. Appl. No. 11/297,225.
Office Action Issued Nov. 25, 2009 in related U.S. Appl. No. 11/297,225.
International Preliminary report on Patentability in related International Application PCT/US05/44410; dated Jan. 17, 2007.
Examination Report and Written Opinion Issued Jun. 27, 2008 in related Singapore Application No. 200704199-9.
Examination Report dated Jul. 7, 2009 in related Singapore Application No. 200704201-3.
Chinese Office Action for the related Chinese Application No. 200680026185.7 dated Mar. 1, 2010.
International Preliminary Report on Patentability for related International Patent Application No. PCT/US05/44411, mailed Oct. 6, 2008.
International Search Report and Written Opinion for related International Patent Application No. PCT/US05/44411, dated Jun. 21, 2007.
International Search Report for related International Patent Application No. PCT/US05/44492 and written opinion; dated May 25, 2006.
International Search Report and Written Opinion for related International Patent Application No. PCT/US08/52427; dated Aug. 4, 2008.
International Search Report and Written Opinion for related International Patent Application No. PCT/US05/44410; dated Jun. 27, 2006.
International Search Report for related International Patent Application No. PCT/US06/27733, dated Apr. 23, 2007.
Office Action for related Chinese Patent Application No. 200580047001.0 issued Jul. 17, 2009.
First Office Action for related Chinese Patent Application No. 200580047294.2; mailed Aug. 21, 2009; 7 pages. (English translation only).
Supplementary Search Report for the related European Application No. 05853353.0 issued Apr. 23, 2010.
Chinese Office Action dated May 25, 2010 in related Chinese Application No. 200580046736.1.
Office Action Issued Jul. 22, 2010 in related U.S. Application No. 11/669,452.
Office Action issued May 10, 2011 in JP Application No. 2007-545641.
Office Action issued May 31, 2011 in JP Application No. 2007-545617.
Office Action issued Jul. 12, 2011 in JP Application No. 2008-522871.

* cited by examiner

AUTO-INJECTION SYRINGE HAVING VENT DEVICE

CROSS REFERENCE TO RELATED APPLICATIONS

This application claims the benefit of U.S. Provisional Application Ser. No. 60/700,219, filed Jul. 18, 2005 and is a continuation-in-part of U.S. Application Ser. No. 11/296,973, filed Dec. 8, 2005, which claims the benefit of priority pursuant to 35 U.S.C. §119(e) of U.S. Provisional Patent Application No. 60/634,486, filed Dec. 9, 2004, the disclosures of which are incorporated by reference herein.

BACKGROUND OF THE INVENTION

1. Field of the Invention

The present disclosure is related to auto-injection syringes. More particularly, the present disclosure is related to an auto-injection syringe having a vent device.

2. Description of Related Art

Diseases such as AIDS, Hepatitis, and others, are increasing within the general population. As a result, there has been a continual trend to institutionalize the use of products that provide protection from the risk of inadvertent needle stick injury. Many prior art devices include self-retracting needles intended to mitigate inadvertent needle stick injuries.

Many life-threatening situations such as allergy-induced anaphylactic shock, and exposure to chemical, radiological, and biological weapons can require the use of auto-injection syringes. Typical auto-injection syringes allow the medically untrained user to automatically inject a medicine by manually trigging the automatic injection. Some prior auto-injection syringes also incorporate self-retracting needles.

The maintenance of the fluid path portion of such devices in a sterile or aseptic condition prior to use has proven difficult in prior devices. Furthermore, the assembly of such devices has proven time consuming and expensive.

Accordingly, there is a continuing need for improved auto-injection syringes that overcome, alleviate, or mitigate one or more of the aforementioned and or drawbacks and deficiencies of the prior art.

BRIEF SUMMARY OF THE INVENTION

It is an object of the present disclosure to provide an auto-injection syringe having a vent device.

It is another object of the present disclosure to provide an easy to assemble auto-injection syringe, where the needle is maintained in a vented sterile and/or aseptic area before assembly of the medicine cartridge in the syringe.

It is yet another object of the present disclosure to provide an auto-injection syringe having an injection assembly and a retraction assembly. The injection and retraction assemblies can be operatively connected to one another by a user. The retraction assembly includes a needle maintained in a vented sterile and/or aseptic area before assembly of the injection and retraction assemblies.

It is still another object of the present disclosure to provide an auto-injection syringe having an injection assembly and a retraction assembly. The injection and retraction assemblies can be operatively connected to one another by a user. The retraction assembly includes an upper seal and a lower seal to define a sterile and/or aseptic area there between. To ease assembly, the upper seal is maintained in place, before use, by a partially biased retraction spring of the retraction assembly. The retraction assembly includes a vent device to equalize pressure between the sterile and/or aseptic area and an exterior of the syringe. In some preferred embodiments, the vent device is defined by a porous plastic end cap of the retraction assembly.

It is a still further object of the present disclosure to provide a retraction assembly for an auto-injection syringe. The retraction assembly includes an upper seal and an end cap. The upper seal is maintained in place, before use, by a partially biased retraction spring. The end cap is defined by a porous plastic material, which allows venting to prevent pressure differences from overcoming the force of the retraction spring and a penetrable elastomeric seal through which the needle element passes upon actuation of the injection mechanism.

The above-described and other features and advantages of the present disclosure will be appreciated and understood by those skilled in the art from the following detailed description, drawings, and appended claims.

DETAILED DESCRIPTION OF THE INVENTION

Figure 1:
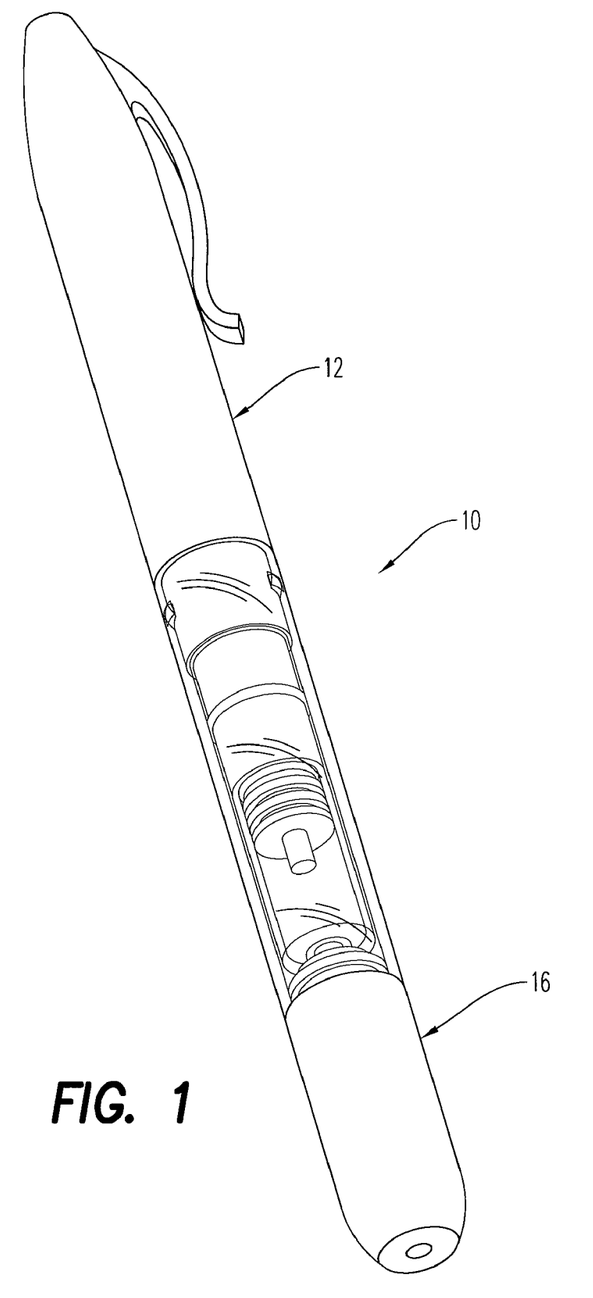
FIG. 1 is a perspective view of an exemplary embodiment of an auto-injection syringe according to the present disclosure.
Figure 2:
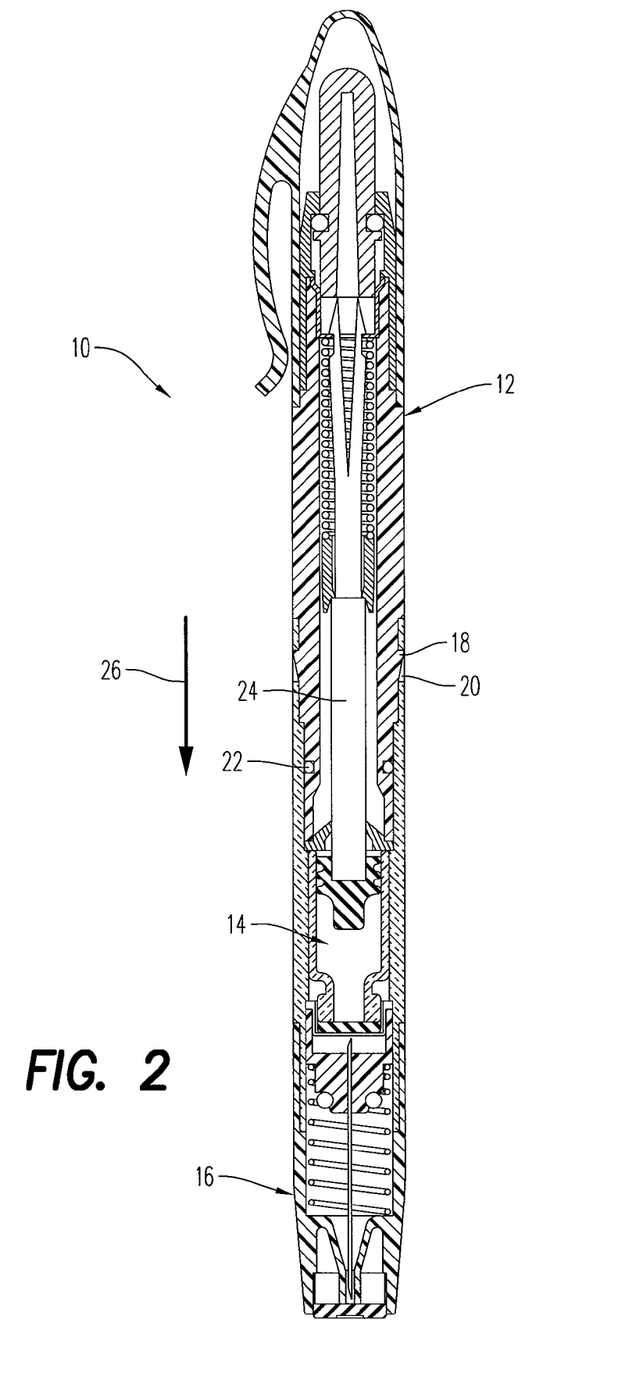
FIG. 2 is a cross sectional view of the syringe of FIG. 1.
Figure 3:
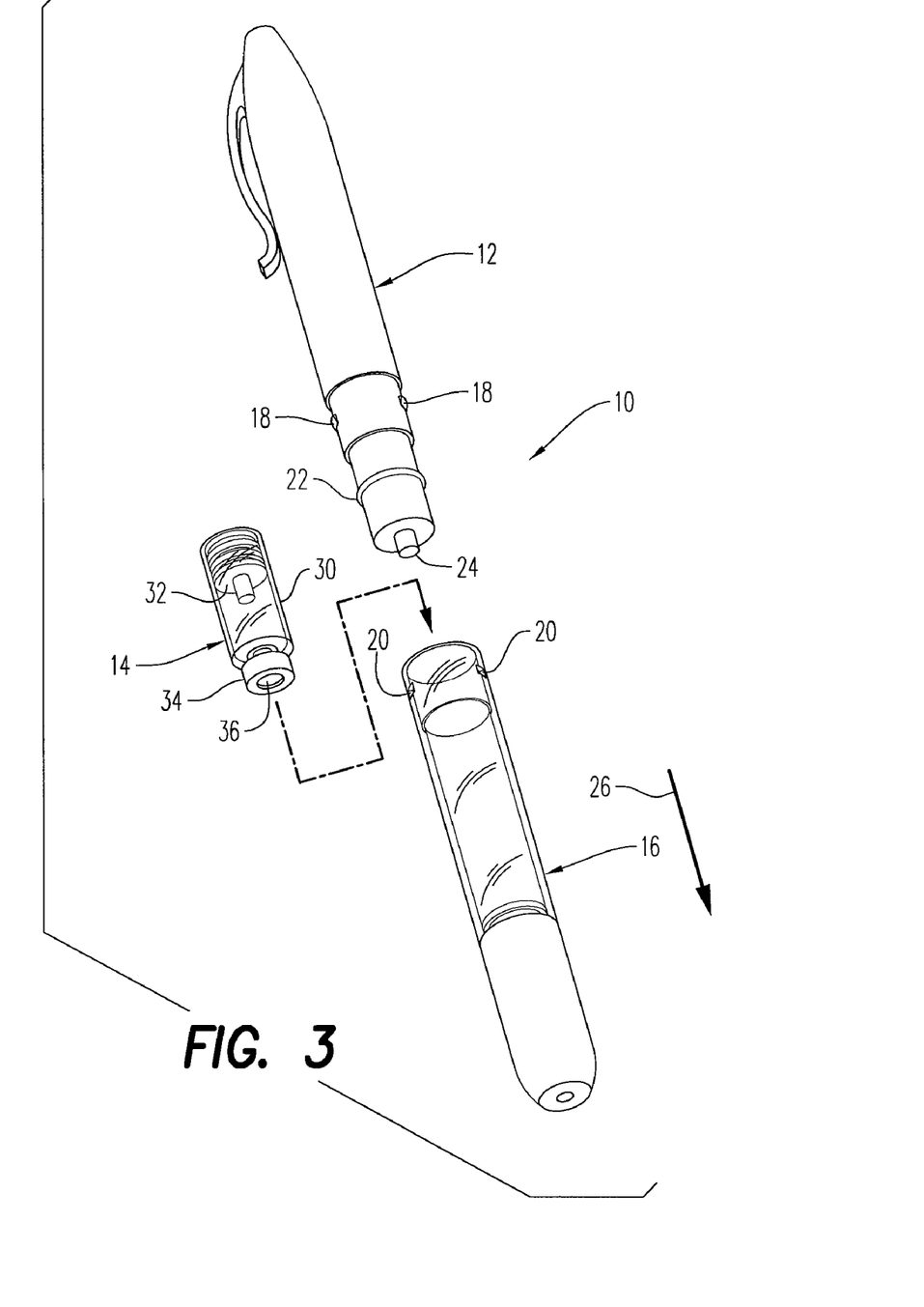
FIG. 3 is a partially exploded view of the syringe of FIG. 1.

Referring to the figures and in particular to FIGS. 1 through 3, an exemplary embodiment of an auto-injection syringe 10 according to the present disclosure is shown. Upon activation, syringe 10 is adapted to automatically extend a hypodermic needle from within the assembly into tissue at an injection site, inject a single, pre-measured dose of medicine, and automatically retract the hypodermic needle into the assembly after the injection is completed.

Advantageously, syringe 10 includes one or more sealed areas comprising a vent device that allows these areas to equalize pressure or vent between the sealed area and the environment exterior to the syringe, while preventing contaminants (e.g., particulate, bacteria, viruses, etc.) from entering the sealed area. It has been determined that the vent device of the present disclosure allows the sealed area to vent when exposed to varying atmospheric conditions present during shipping and, often times when carried or stored by the user. In addition, the vent device of the present disclosure can advantageously allow the syringe to be sterilized using processes such as, but not limited to, exposure to ethylene oxide (EtO) gas, gamma irradiation, steam, dry heat, and others.

Syringe 10 includes an injection assembly 12, a medicine cartridge 14, and a retraction assembly 16. Thus, syringe 10 is a multi-component device that can be quickly and easily assembled by a user or a health care provider (e.g., pharmacist, doctor, nurse, etc) as needed. Since syringe 10 does not require assembly at the time of manufacture, the present disclosure effectively separates expiry of medicine cartridge 14 from the expiry of syringe 10.

For example, typical flu vaccines have an expiration date of one year. Although the benefits afforded the public of having a means for self-inoculation are self-evident as compared to waiting in line at a clinic and paying for travel and the cost of an office visit, it is difficult at the time of manufacture to accurately forecast the severity of the flu season and, thus, the anticipated demand for devices loaded with vaccine. Thus, if the entire device was pre-assembled including the medicine cartridge as is often required with other devices, and the severity of the flu season was less than anticipated; the cost of vaccine expiration would be excessive, given that the entire device would be rendered obsolete. Conversely, in the case of the present invention, medicine cartridge 14 can be kept separate from syringe 10 until the demand is realized. Thus, the user or health care provider can maintain a supply of injection and retraction assemblies 12, 16, which have a much longer useful life, while only replacing any expired medicine cartridges 14.

In the illustrated embodiment, injection assembly 12 and retraction assembly 16 can be secured to one another in a snap fit manner so that the assemblies can not be removed from one another after injection. For example, injection assembly 12 can include one or more radially protruding tabs 18 that cooperate in an interference relationship with a corresponding number of openings 20 defined in retraction assembly 16. As injection assembly 12 is inserted into retraction assembly 16, tabs 18 act on the retraction assembly to deform the inner dimension of the tube. Once tabs 18 are received by openings 20, the inner dimension of retraction assembly 16 returns to its original dimension, by its own resiliency, to permanently secure the tabs within the openings.

Of course, it is contemplated by the present disclosure for injection assembly 12 and retraction assembly 16 to be secured to one another in any desired manner and, preferably, so that the assemblies can not be removed from one another after injection.

In the assembled state, injection assembly 12 and retraction assembly 16 define a hermetic or air tight seal therebetween. For example, injection assembly 12 can include a sealing member 22 such as, but not limited to, an o-ring. Once injection assembly 12 and retraction assembly 16 are axially assembled and secured together, sealing member 22 cooperates with the interior of the retraction assembly and the exterior of injection assembly to form a hermetic radial seal therebetween. In the illustrated embodiment, sealing member 22 is positioned internal to openings 20 defined in retraction assembly 16 to provide the hermetic seal below the snap fit connection between tabs 18 and openings 20. Thus, the area exterior to the medicine cartridge 14 and internal to the syringe 10 are hermetically sealed from one another by the interaction of sealing member 22 and retraction/injection assemblies 16, 18.

Generally, injection assembly 12 includes an injection spring. Retraction assembly 16 receives medicine cartridge 14 and includes a hypodermic needle and a retraction spring. Upon activation of the injection assembly 12, the spring force of the injection spring, overcomes the force of the retraction spring to insert the needle into the tissue at the injection site, places the medicine cartridge in fluid communication with the needle, and dispenses the medicine from the cartridge. Once the medicine has been injected, injection assembly 12 automatically disconnects the injection spring so that the retraction spring can withdraw the needle back into retraction assembly 16.

For purposes of clarity, the detailed operation of injection assembly 12 is not described herein. Rather, injection assembly 12 can operate in any known manner to inject medicine from cartridge 14 intramuscularly, subcutaneously and/or intradermally by driving a plunger rod 24 in an injection direction 26 as seen in FIGS. 2 and 3. For example, injection assembly 12 can operate in the manner shown and described in commonly owned and assigned U.S. Pat. No. 6,387,078, the content of which is incorporated in its entirety by reference herein.

As discussed above, syringe 10 does not require assembly at the time of manufacture. The assembly of syringe 10 is discussed with reference to FIG. 3. Cartridge 14 includes a medicine vial 30, a movable stopper 32, and a crimp cap 34. Cap 34 includes a pierceable member 36.

Cartridge 14 is inserted into retraction assembly 16 so that movable stopper 32 is proximate to injection assembly 12, while cap 34 and pierceable member 35 are adjacent the lower portion of retraction assembly 16.

Figure 4:
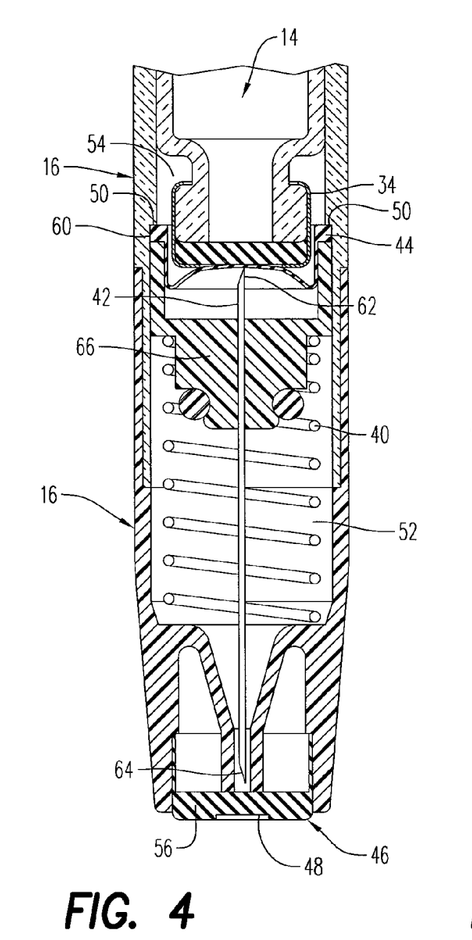
FIG. 4 is a sectional view of an exemplary embodiment of a retraction assembly according to the present disclosure before injection.
Figure 5:
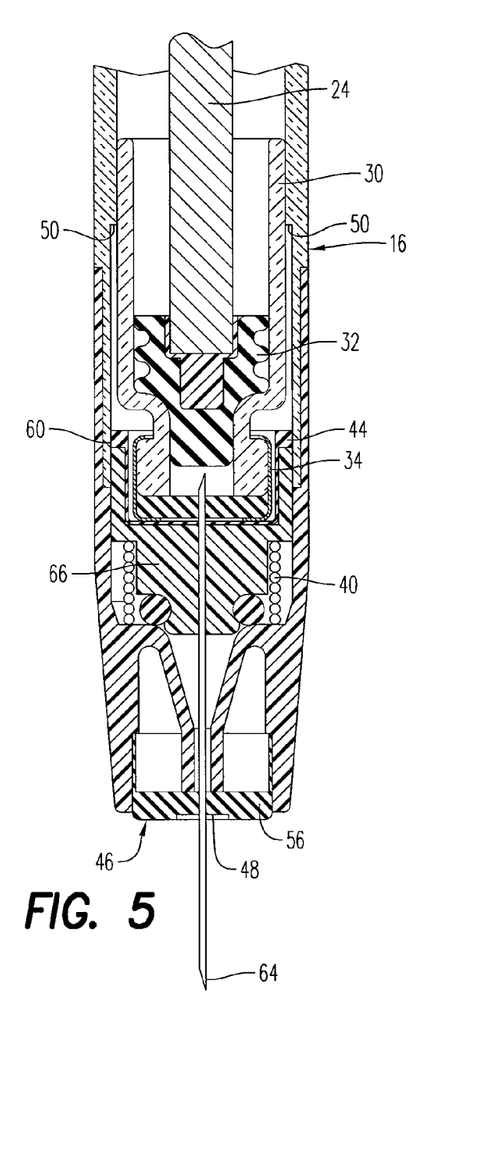
FIG. 5 is a sectional view of the retraction assembly of FIG. 4, during injection and before retraction.

Once cartridge 14 is installed in retraction assembly 16, the injection and retraction assemblies can be operatively secured to one another. Upon assembly, plunger rod 24 resides just proximal to stopper 32 and cap 34 resides in contact with an upper seal 44 (FIGS. 4 and 5). In the assembled position, activation of injection assembly 12 causes plunger rod 24 to first move medicine cartridge 14 and then stopper 32 in injection direction 26 and, thus, to insert the needle and expel medicine contained therein from the cartridge, respectively.

Retraction assembly 16 is described with reference to FIGS. 4 and 5. Retraction assembly 16 includes a retraction spring 40, a double-ended needle 42, an upper seal 44, an end cap 46, and a lower seal 48.

Upper seal 44 is configured to receive cap 34 of cartridge 14. Upper seal 44 is configured to form a hermetic seal against a facial sealing surface 50 and/or a radial sealing surface 60 defined in retraction assembly 16.

Before activation of syringe 10, retraction spring 40 is maintained in a partially compressed position between a needle hub 66 and end cap 46. In this position, retraction spring 40 urges needle hub 66 in a direction opposite injection direction 26 to maintain upper seal 44 in contact with and, thus, sealed against sealing surface 50. Advantageously, retraction assembly 16 can be terminally sterilized during manufacture so that a sterile or aseptic (hereinafter "sterile") interior area 52 is defined between upper and lower seals 44, 48. In this manner, interior area 52 maintains needle 42 in a sterile or aseptic condition before activation of syringe 10.

It has been determined that without the capability to adjust to pressure differential between the interior area 52 and exterior 54, the pressure differential can, in some instances, overcome the force of spring 40 such that the contact between upper seal 44 and sealing surface 50 may be broken. Interrupting the contact between upper seal 44 and its sealing surface 50 may compromise the sterility or aseptic condition of interior area 52.

For example, retraction assembly 16 (before assembly with injection assembly) can be exposed to temperature and/or pressure changes during manufacturing, shipping, or during storage. These changes in environmental conditions can be sufficient to cause a lower pressure within interior area 52 as compared to an exterior 54 of retraction assembly. Alternately, these changes in environmental conditions can be sufficient to cause a higher pressure at exterior 54 as compared to that in interior area 52. The pressure difference between interior area 52 and exterior 54 can be sufficient to overcome the force of spring 40 and, thus, to break the contact between upper seal 44 and sealing surface 50 and/or to cause the upper seal to deflect in injection direction 26, potentially becoming punctured by medicine entrance tip 62 of needle 42.

To address the disadvantages associated with changes in differential pressure between interior area 52 and exterior 54, retraction assembly 16 advantageously includes a vent device 56. Vent device 56 places interior area 52 in fluid communication with exterior 54 so that the interior area can exchange gas with the exterior. Preferably, vent device 56 is a microbial filter so that interior area 52 can exchange gas with exterior 54 without allowing microbes, particulate, bacteria, viruses and the like to enter and potentially contaminate the interior area. By allowing for gas exchange between interior area 52 and exterior 54, vent device 56 ensures that upper seal 44 remains in contact with sealing surface 50.

In one embodiment, end cap 46 is configured as vent device 56. For example, end cap 46 can be made of a thermoplastic material having sufficient porosity to allow for pressure equalization (hereinafter "venting") of interior area 52, while preventing contaminants (e.g., microbes, particulate, bacteria, viruses, etc.) from entering the area. Thermoplastic materials having the aforementioned venting and sterility/aseptic barrier capabilities are shown and described in U.S. Pat. No. 6,551,608 to Porex Technologies Corporation of Fairburn, Georgia.

In this embodiment, end cap 46 functions as vent device 56. Here, end cap 46 is preferably a rigid thermoplastic material molded or otherwise formed in the desired shape. End cap 46 maintains lower seal 48 in a desired position with respect to needle 42. For example, end cap 46 can be co-molded with lower seal 48 to form a unitary element.

It should be recognized that syringe 10 is described by way of example having vent device 56 at end cap 46. Of course, it is contemplated by the present disclosure for any portion of retraction assembly 16 in fluid communication with interior area 52 and the exterior 54 of the retraction assembly to include vent device 56.

Advantageously, the inclusion of vent device 56 in auto-injection syringe 10 assists in maintaining the sterile and/or aseptic condition of interior area 52 during manufacturing, shipping, and storage.

Referring again to FIGS. 4 and 5, needle 42 is a double-ended hypodermic needle that includes a medicine entrance tip 62 and a tissue penetrating and medicine exit tip 64. Entrance tip 62 is positioned proximate to upper seal 44, while exit tip 64 is positioned proximate to lower seal 48 as shown in FIG. 4.

During use of syringe 10, the movement of plunger rod 24 urges medicine cartridge 14 in injection direction 26 towards upper seal 44 so that entrance tip 62 pierces the upper seal and pierceable member 36 of the cartridge to place the needle in fluid communication with the cartridge 14. Because the medicament within medicine cartridge 14 is an incompressible fluid, further movement of plunger rod 24 also urges needle 42 in injection direction 26 by overcoming the force of retraction spring 40. Thus, exit tip 64 pierces lower seal 48 and is inserted into the tissue at the injection site. Finally, the movement of plunger rod 24 urges stopper 32 in injection direction 26 so that medicine in cartridge 14 is expelled into the user through exit tip 64 as shown in FIG. 5.

Once injection assembly 12 completes movement of plunger rod 24, the plunger rod is released from its injection spring (not shown) so that retraction spring 40 can urge needle 42, cartridge 14, and the plunger rod in a direction opposite injection direction 26 until the exit tip 64 is retracted back into interior area 52 of retraction assembly 16.

In the embodiment where injection assembly 12 is permanently secured to retraction assembly 16, retraction of needle 42 into the retraction assembly renders syringe 10 safe from inadvertent puncture by the needle and, thus, safe for disposal.

Advantageously, retraction assembly 16 defines interior area 52 having double ended needle 42 sealed therein. Here, the double-ended needle 42 can be maintained in a sterile or aseptic condition regardless of the changing environmental conditions by vent device 56.

Syringe 10 can be provided in an unassembled state in a terminally sterilized kit (not shown) for assembly and use. Here, the kit can include injection assembly 12 and retraction assembly 16 in a sterilized package. Thus, the kit allows a user or medical provider to prepare syringe 10 for use by simply opening the package, placing a separately supplied medicine cartridge 14 in retraction assembly 16, and securing the injection and retraction assemblies to one another. In some embodiments, the kit can include one or more injection site cleaning swabs, such as pre-packaged alcohol swabs, in the sterilized package. In other embodiments, the kit can include medicine cartridge 14 in the sterilized package.

It should also be noted that the terms first, second, third, upper, lower, and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. An auto-injection syringe comprising:
 a retraction assembly having:
  a hypodermic needle and a needle hub connected to the hypodermic needle,
  an upper seal urged against and in contact with a distally facing sealing surface perpendicular to a radial sealing surface of an inner diameter of said retraction assembly by a force of a retraction spring on said needle hub, and
  a lower seal, wherein the upper seal and the lower seal define a sealed area, and
  wherein the hypodermic needle and the needle hub connected to the hypodermic needle are maintained in the sealed area within said retraction assembly; and
 a vent device in fluid communication between said sealed area for equalizing pressure between said sealed area and an exterior of said retraction assembly, wherein said vent device is a microbial filter.

2. The syringe of claim 1, further comprising an injection assembly operatively connectable to said retraction assembly.

3. The syringe of claim 2, further comprising a medicine cartridge being operatively insertable into said retraction assembly.

4. The syringe of claim 1, wherein said upper seal is maintained in a sealing relation with said retraction assembly by a partially biased retraction spring.

5. The syringe of claim 1, wherein said lower seal comprises a penetrable elastomeric seal through which a portion of said hypodermic needle can pass.

6. The syringe of claim 1, wherein said vent device comprises a porous plastic end cap.

7. The syringe of claim 6, wherein said porous plastic end cap further comprises a penetrable elastomeric seal through which a portion of said hypodermic needle can pass.

8. The syringe of claim 1, wherein said sealed area is sterile.

9. An auto-injection syringe comprising:
an injection assembly; and
a retraction assembly being operatively securable to said injection assembly, said retraction assembly comprising:
   a hypodermic needle having a needle hub,
   an end cap having a lower seal through which a portion of said hypodermic needle can pass;
   a retraction spring disposed between said needle hub and said end cap and maintained in a partially compressed condition therebetween,
   an upper seal urged against and in contact with a distally facing sealing surface of said retraction assembly by the force of said retraction spring on said needle hub so that a sealed area is defined between said upper and lower seals, said hypodermic needle and needle hub being disposed in said sealed area; and
   a vent device in fluid communication with said sealed area for pressure equalization between said sealed area and an exterior of said retraction assembly, wherein said vent device is a microbial filter.

10. The syringe of claim 9, further comprising a medicine cartridge for receipt in said injection and retraction assemblies when said assemblies are secured to one another.

11. The syringe of claim 9, further comprising an o-ring member forming a hermetic seal between said retraction assembly and said injection assembly when said retraction assembly is operatively secured to said injection assembly.

12. The syringe of claim 9, wherein said end cap comprises a thermoplastic material having sufficient porosity to allow for said pressure equalization so that said end cap is said vent device.

13. The syringe of claim 9, wherein said sealed area is sterile.

14. An injection kit comprising:
an injection assembly;
a retraction assembly having:
   a hypodermic needle and a needle hub connected to the hypodermic needle,
   an upper seal urged against and in contact with a distally facing sealing surface perpendicular to a radial sealing surface of an inner diameter of said retraction assembly by a force of a retraction spring on said needle hub, and
   a lower seal, wherein the upper seal and the lower seal define a sealed area, and
   wherein the hypodermic needle and the needle hub connected to the hypodermic needle are maintained in the sealed area within said retraction assembly, said retraction assembly being operatively connectable to said injection assembly; and
a vent device in fluid communication with said sealed area for equalizing pressure between said sealed area and an exterior of said retraction assembly, wherein said vent device is a microbial filter.

15. The injection kit of claim 14, wherein said retraction assembly further comprises an end cap having the lower seal through which a portion of said hypodermic needle can pass; wherein the retraction spring is disposed between said needle hub and said end cap and maintained in a partially compressed condition therebetween.

16. The injection kit of claim 15, further comprising a medicine cartridge for receipt in said injection and retraction assemblies when said assemblies are secured to one another.

17. The injection kit of claim 15, further comprising at least one injection site cleaning swab.

18. The injection kit of claim 15, further comprising an adhesive bandage.

19. The injection kit of claim 16, further comprising a package containing said injection and retraction assemblies.

20. The injection kit of claim 19, wherein said package is terminally sterilized.

* * * * *